(12) United States Patent
Knodel et al.

(10) Patent No.: US 7,001,408 B2
(45) Date of Patent: Feb. 21, 2006

(54) SURGICAL DEVICE WITH EXPANDABLE MEMBER

(75) Inventors: Bryan D. Knodel, Flagstaff, AZ (US); Timothy B. Knodel, Flagstaff, AZ (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 383 days.

(21) Appl. No.: 10/247,916

(22) Filed: Sep. 20, 2002

(65) Prior Publication Data
US 2004/0059374 A1 Mar. 25, 2004

(51) Int. Cl.
*A61B 17/28* (2006.01)

(52) U.S. Cl. ....................... 606/207; 606/205
(58) Field of Classification Search ............. 606/207, 606/205–206, 219, 142, 191–195, 198; 227/175.2, 227/175.1, 176.1, 180.1
See application file for complete search history.

(56) References Cited

U.S. PATENT DOCUMENTS

| | | | |
|---|---|---|---|
| 4,505,414 A | 3/1985 | Filipi | |
| 4,605,004 A | 8/1986 | Di Giovanni et al. | |
| 4,754,909 A | 7/1988 | Barker et al. | |
| 5,047,039 A | 9/1991 | Avant et al. | |
| 5,236,438 A * | 8/1993 | Wilk | 606/215 |
| 5,258,008 A | 11/1993 | Wilk | |
| 5,452,832 A | 9/1995 | Niada | |
| 5,553,765 A | 9/1996 | Knodel et al. | |
| 5,597,107 A | 1/1997 | Knodel et al. | |
| 5,637,110 A | 6/1997 | Pennybacker et al. | |
| 5,673,840 A | 10/1997 | Schulze et al. | |
| 5,697,432 A | 12/1997 | Yun et al. | |
| 5,709,680 A | 1/1998 | Yates et al. | |
| 5,732,872 A | 3/1998 | Bolduc et al. | |
| 5,769,303 A | 6/1998 | Knodel et al. | |
| 5,769,848 A * | 6/1998 | Wattanasirichaigoon | 606/46 |
| 5,779,131 A | 7/1998 | Knodel et al. | |
| 5,779,132 A | 7/1998 | Knodel et al. | |
| 5,810,855 A | 9/1998 | Rayburn et al. | |
| 5,839,639 A | 11/1998 | Sauer et al. | |
| 5,947,363 A | 9/1999 | Bolduc et al. | |
| 5,951,576 A | 9/1999 | Wakabayashi | |
| 6,032,849 A | 3/2000 | Mastri et al. | |
| 6,096,037 A * | 8/2000 | Mulier et al. | 606/49 |
| 6,264,084 B1 | 7/2001 | Hayes | |
| 2001/0010320 A1 | 8/2001 | Bolduc et al. | |
| 2001/0016749 A1 | 8/2001 | Blatter et al. | |

OTHER PUBLICATIONS

EPO Examination Report dated Nov. 11, 2004 for Application No. 03255873.6.

* cited by examiner

*Primary Examiner*—(Jackie) Tan-Uyen T. Ho

(57) ABSTRACT

A surgical device for manipulating tissue. The device includes an elongated shaft having a proximal end and a distal end extending therefrom. There is also an elongated end effector having a proximal end attached to the distal end of the shaft, a distal end extending therefrom. The end effector has first and second opposing jaws which are movable with respect to each other from an open position, wherein the jaws are spaced apart, to a closed position wherein the jaws are in close approximation to one another. At least one of the jaws has an expandable member disposed thereon for selectively increasing the size of the jaw in a direction perpendicular to the longitudinal axis so as to increase the rigidity of the end effector.

5 Claims, 6 Drawing Sheets

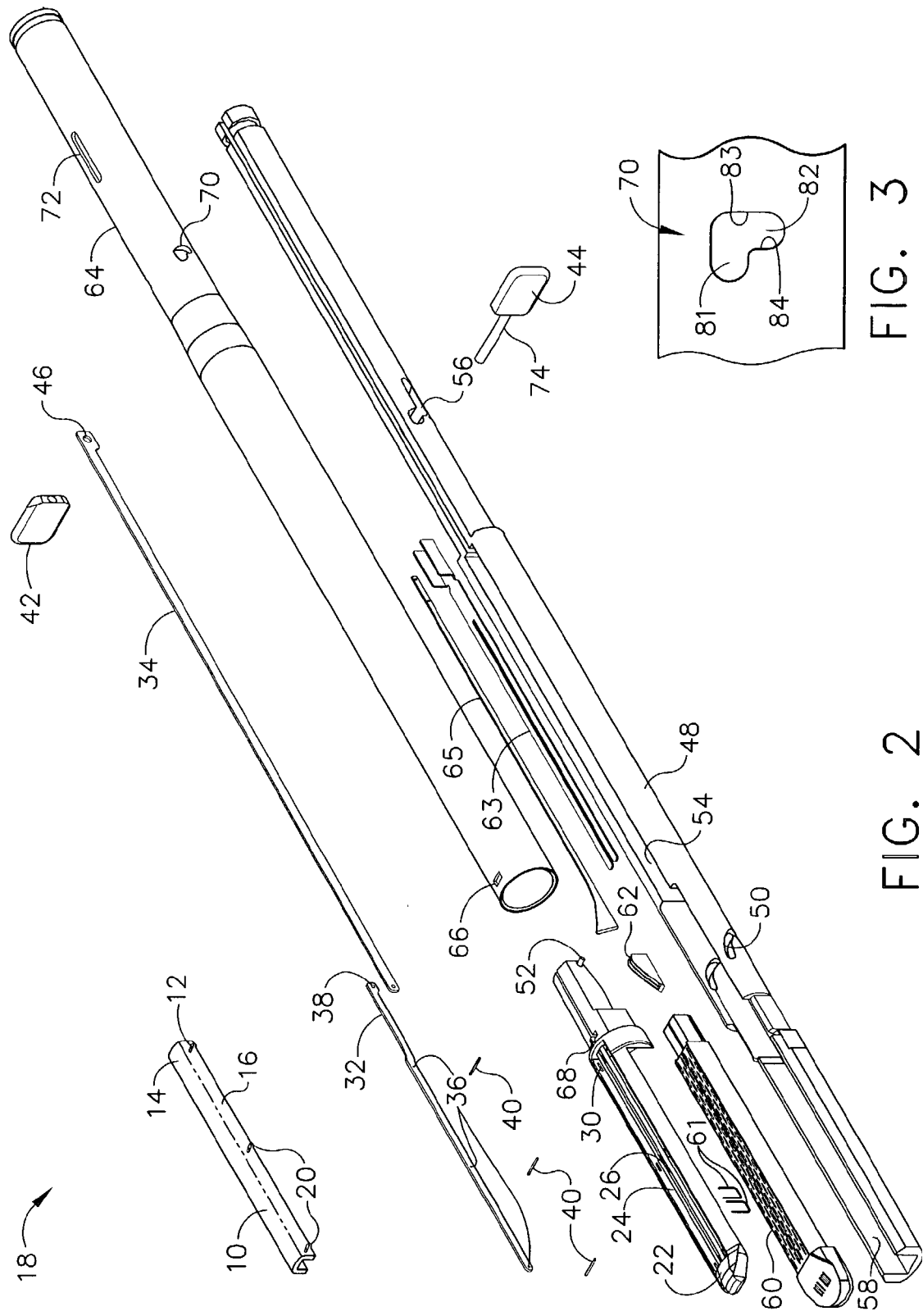

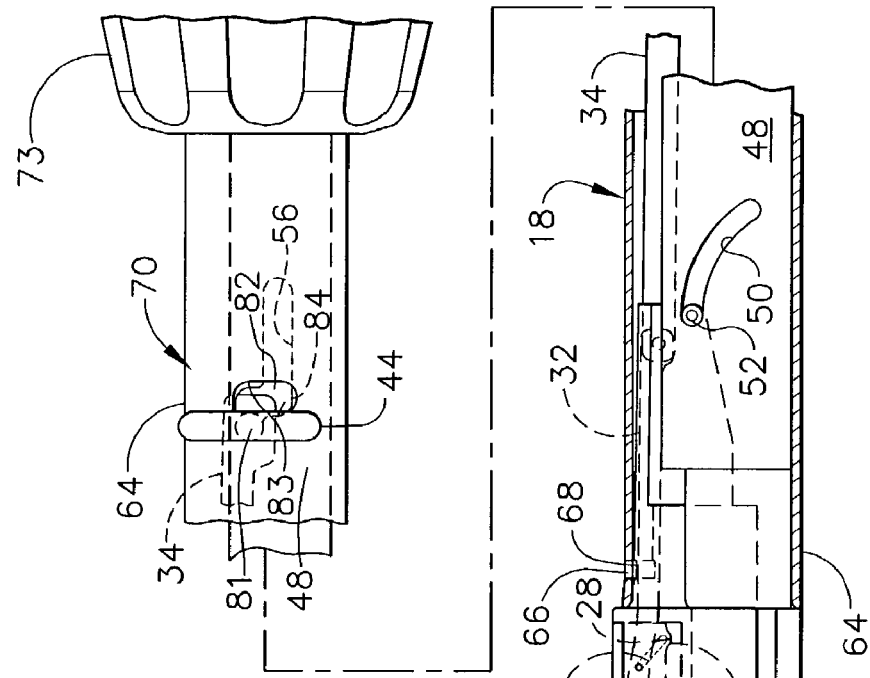
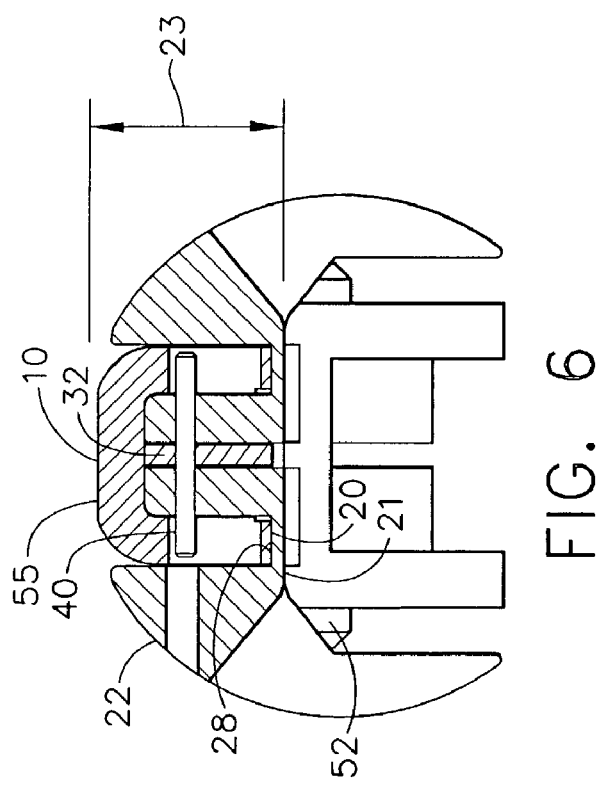
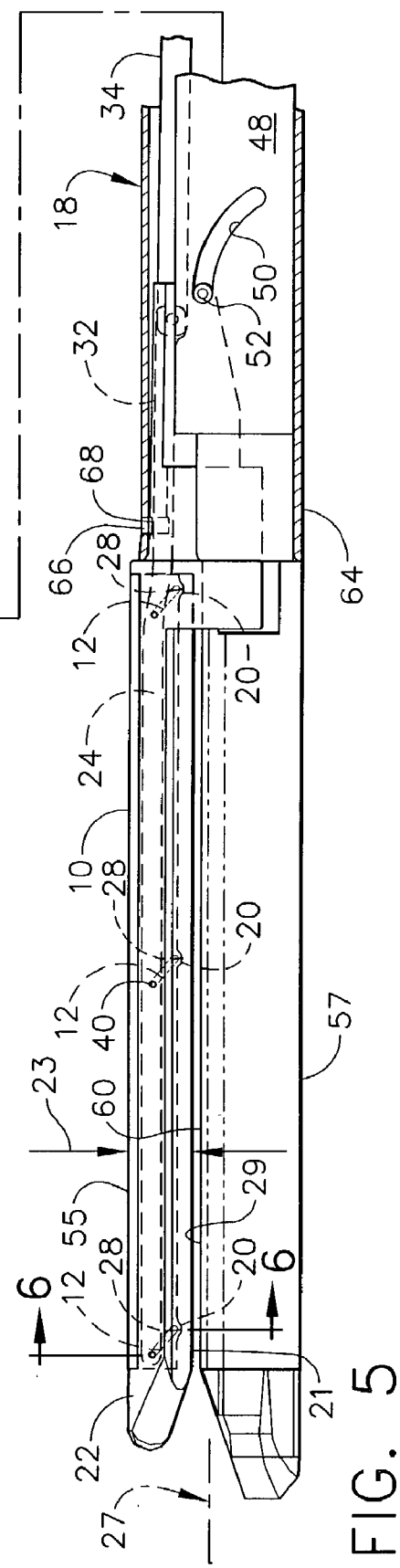
FIG. 6
FIG. 5

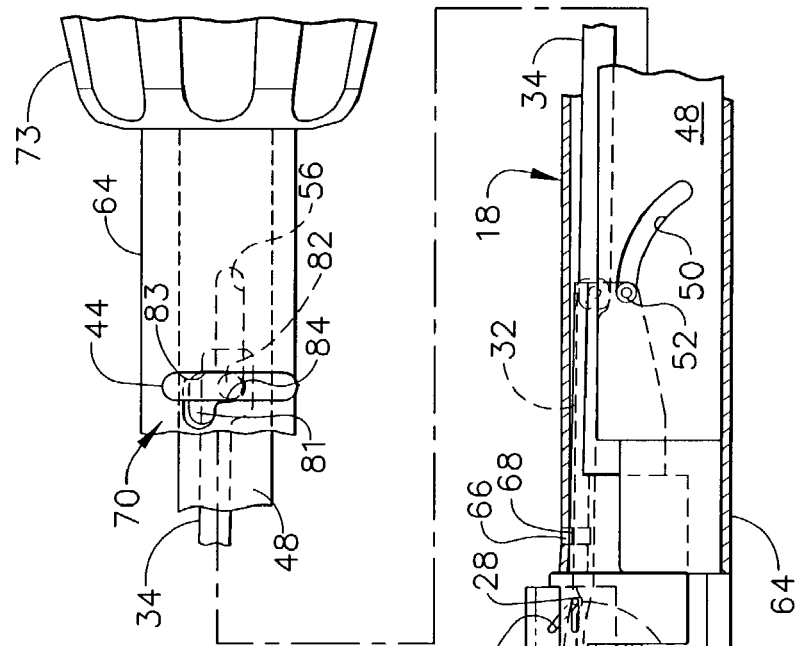
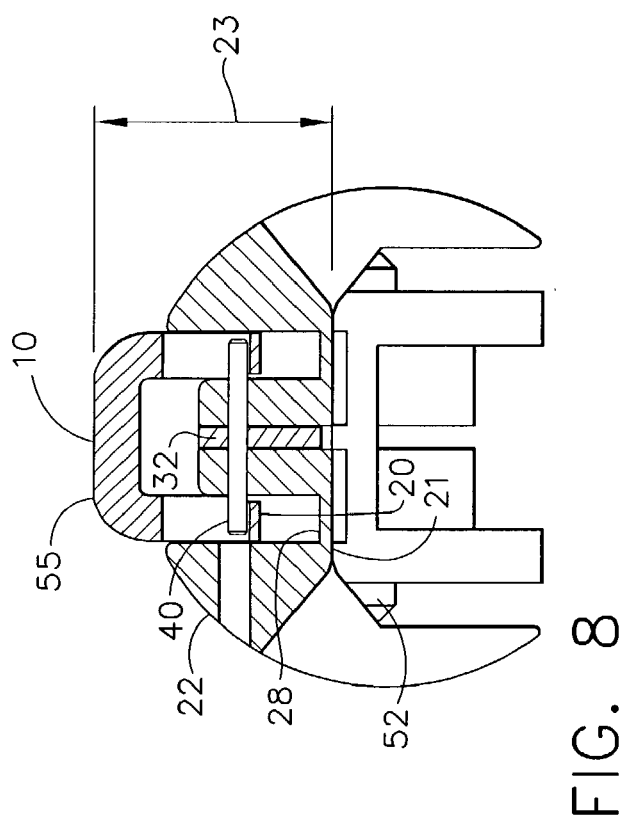

SURGICAL DEVICE WITH EXPANDABLE MEMBER

This application is related to the copending U.S. patent application Ser. No. 10/247,897, which is hereby incorporated herein by reference.

FIELD OF THE INVENTION

The present invention has application in conventional endoscopic and open surgical instrumentation as well as application in robotic or power assisted surgery. The present invention relates, in general, to an expandable member to stiffen a jaw of a surgical device and, more particularly, to an anvil cap movable to a position to increase the height of an anvil of an endoscopic linear cutter.

BACKGROUND OF THE INVENTION

Medical devices to simultaneously cut and staple tissue in a surgical patient, often called linear cutters, are commonly used in endoscopic surgery. In endoscopic surgery, linear cutters are placed into the patient through a cannula having a small orifice. Each linear cutter generally has an endeffector in the form of a cartridge, for holding and ejecting staples, and an anvil, for forming the ejected staple into the proper shape. After passing through the cannula, the cartridge and anvil are clamped around tissue to be cut and stapled to compress the tissue and stem blood flow. The tissue exerts a reactive force against the cartridge and the anvil of the device. Examples of linear cutters can be found in U.S. Pat. Nos. 6,032,849 and 5,673,840, both of which are hereby incorporated herein by reference.

An anvil of a linear cutter has depressions positioned within it. Each depression receives the legs of a "C" shaped staple ejected towards it and bends the legs of the staples to form "B" shaped closures. To keep each pocket positioned in the correct position and at the correct distance from the cartridge, it is advantageous to minimize anvil deflection. Force exerted against the anvil from the tissue causes bending of the anvil and channel of the end-effector in a plane orthogonal to the tissue surface. The bending displaces the staple-forming portion of the anvil from the optimum position to receive an ejected staple, and may result in malformation of staples. The malformation has a greater potential for occurring when the cartridge and the anvil of the device are made longer.

A technique for creating a stiffer anvil is to increase the dimension of the anvil in the plane of bending. This dimension is commonly called the height of the anvil, and increasing the height of the anvil can also enlarge the crosssectional area of the anvil. However, the benefits of endoscopic surgery stem from creating small incisions on the patient. Small incisions use small cannulas, and a small cross-sectional area for the anvil is desirable to fit the jaws of the device through a small cannula. Longer working jaws are desirable, but jaw length has been limited by the need to maintain small cross-sectional area and efficacious staple formation. Deflection needs consideration not only in the design of endoscopic linear cutters, but also in any endoscopic device having an attached implement that receives a reactive force from tissue or the work being performed.

Because of the benefits of a small incision, there has been a desire to use an implement that will have a short height to facilitate entry through a small orifice and that will expand to a greater height to become more rigid while being used inside the body. The present invention provides for a surgical device having a working implement with a movable device that can be raised to increase the implement rigidity, and that can be lowered to decrease implement height to facilitate insertion through a cannula.

SUMMARY OF THE INVENTION

In accordance with the present invention, there is provided a surgical device for manipulating tissue. The device includes an elongated shaft having a proximal end and a distal end extending therefrom. There is also an elongated end effector having a proximal end attached to the distal end of the shaft, a distal end extending therefrom. The end effector has first and second opposing jaws which are movable with respect to each other from an open position, wherein the jaws are spaced apart, to a closed position wherein the jaws are in close approximation to one another. At least one of the jaws has an expandable member disposed thereon for selectively increasing the size of the jaw in a direction perpendicular to the longitudinal axis so as to increase the rigidity of the end effector.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 2 is an isometric exploded view of the shaft of the linear cutter of FIG. 1.

FIG. 3 is a fragmentary side elevation view of a slot within the tube shown in FIG. 2.

FIG. 5 is a side elevation view, partially in section, of the shaft of the linear cutter of FIG. 1 showing the anvil closed against the cartridge and the anvil cap lowered into a cavity of the anvil.

FIG. 6 is a section view taken along line 6—6 of FIG. 5 depicting the anvil cap lowered into a cavity of the anvil.

FIG. 7 is a side elevation view, partially in section, of the shaft of the linear cutter of FIG. 1 showing the anvil closed against the cartridge and the anvil cap raised from the cavity of the anvil.

FIG. 8 is a section view taken along line 8—8 of FIG. 7 depicting the anvil cap raised from the cavity of the anvil.

DETAILED DESCRIPTION OF THE INVENTION

Figure 1:
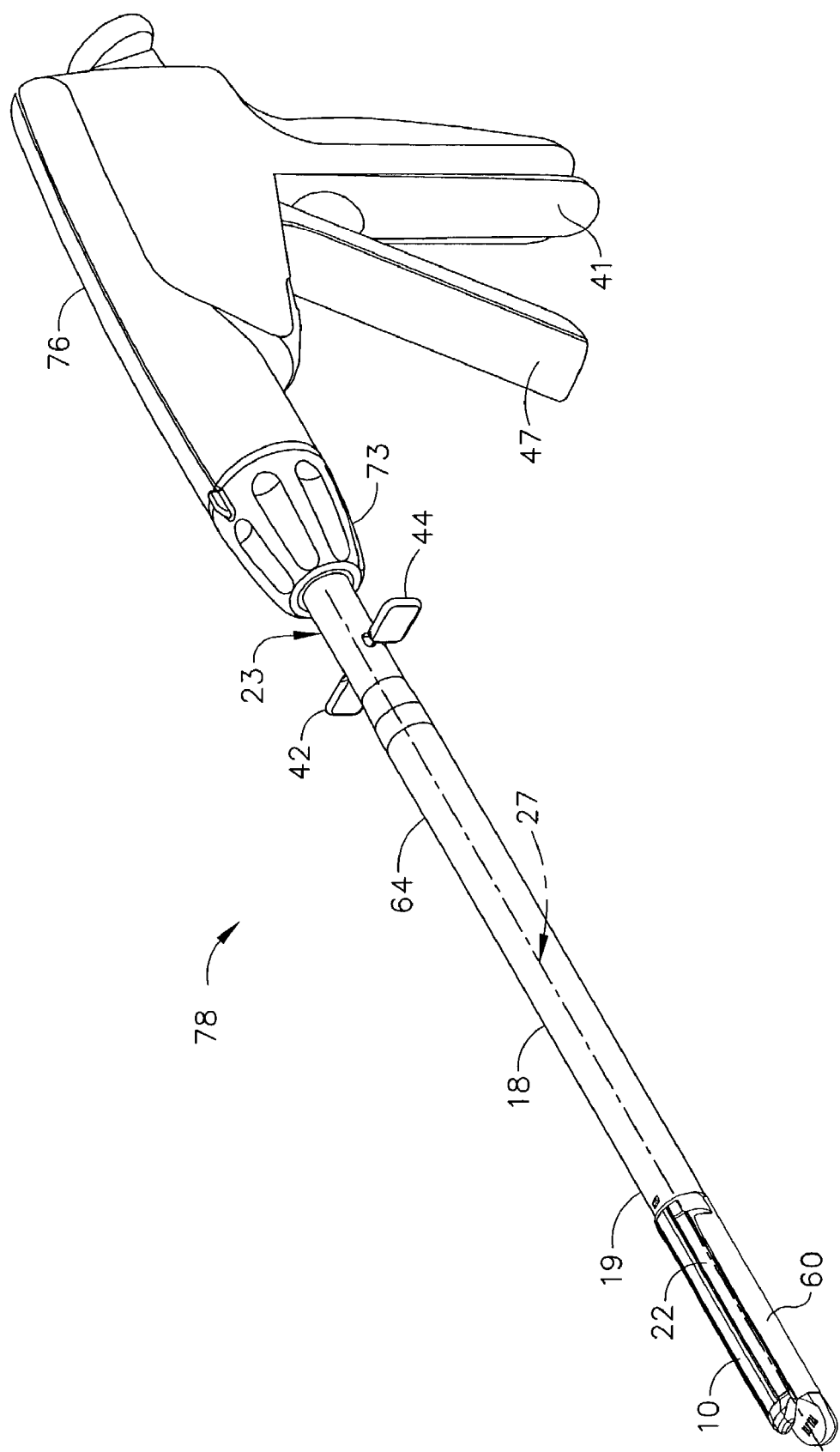
FIG. 1 is an isometric view of an endoscopic linear cutter having an expandable member according to an embodiment of the invention.

FIG. 1 shows a surgical device 78 for manipulating tissue. Surgical device 78 has a first and a second jaw, and one of the jaws is equipped with an expandable member according to an embodiment of the invention. In the embodiment shown in FIG. 1, the expandable member is an anvil cap 10. Anvil cap 10 is shown on one of the jaws, anvil 22, which is closed adjacent to a second jaw, or cartridge 60. Cartridge 60 contains staples 61 (FIG. 2), which can be ejected into tissue to be formed into shape to join and retain the tissue by pockets within anvil 22. Anvil 22 and cartridge 60 are located at a distal end 19 of an elongated shaft 18. Shaft 18 in the embodiment depicted further comprises a tube 64 extending along a longitudinal axis 27 proximally towards a rotation knob 73 and a handle 76. Handle 76 attaches at a proximal end 23 of shaft 18. Right thumbpad 42 and left thumbpad 44 extend from shaft 18, as an expander actuator, to be grasped by a physician to expand anvil 22, as will be shown.

In the embodiment depicted in FIG. 1, surgical device 78 is an endoscopic linear cutter. An endoscopic cutter suitable for modification with the addition of anvil cap 10 could be one described in U.S. Pat. No. 5,597,107 issued to Bryan Knodel et al, on Jan. 28, 1997, and which is hereby incorporated herein by reference. Handle 76 can be the handle of the endoscopic linear cutter described in U.S. Pat. No. 5,597,107, and contains actuators to move portions of shaft 18. A closure actuator 41 within handle 76 can move tube 64 to drive anvil 22 to positions next to and away from cartridge 60. A firing actuator 47 within handle 76 can be used to eject staples 61 into tissue.

FIG. 2 shows an exploded isometric view of a shaft 18 of surgical device 78. Anvil cap 10 is a substantially rigid member used to stiffen anvil 22. Anvil cap 10 is a roughly "U" shaped device having a horizontal section 14 and two vertical sections 16. Anvil cap 10 has the inside of the "U" shape open towards anvil 22 and three diagonal cap slots 12, cut into each vertical section 16. The length of each cap slot 12 extends at a diagonal to longitudinal axis 27 (FIG. 1) of shaft 18. The distal portion of each cap slot 12 is closer to the closed, section of the "U" than the proximal portion. A bulge 20 rises on vertical section 16 next to each cap slot 12, along the narrow material edge of the open side of the "U."

Cavity 24 receives anvil cap 10 into anvil 22. A linkage 32 extends through the center of cavity 24. Linkage 32 has three anvil holes 36 to align with cap slots 12, and also provides a linkage hole 38 at a proximal end. Linkage actuator 34 attaches at linkage hole 38 using, for example, a pin, and extends proximally through shaft 18 to a thumbpad hole 46 at the proximal end of linkage actuator 34. Linkage 32 can rotate relative to linkage actuator 34 about linkage hole 38 to facilitate rotational motion of anvil 22.

Channel 48 carries anvil 22 with assembled anvil cap 10, linkage 32 and linkage actuator 34. Channel 48 also carries a knife 65 and a wedge driver 63. Curvilinear slots 50 retain anvil bosses 52 to locate anvil 22. Anvil bosses 52 are free to translate along the curve of curvilinear slots 50. Two "Z" shaped channel thumbpad slots 56 are located near the proximal end of Channel 48, and at its distal end, channel 48 has a cartridge retention area 58.

Cartridge 60 assembles to cartridge retention area 58. Cartridge 60 supplies staples 61 and staple drivers (not shown) to surgically staple tissue. Firing wedge 62 travels through openings (not shown) within cartridge 60, forcing staple drivers towards the tissue surface and forcing staples 61 into tissue.

Tube 64 encloses the proximal end of channel 48, linkage actuator 34, and the proximal end of linkage 32. An indentation 66 in tube 64 near the distal end of tube 64 fits into groove 68 on anvil 22. Tube thumbpad slots 70 are near the proximal end of tube 64 and have a roughly "L" shaped configuration.

Right thumbpad 42 and left thumbpad 44 are assembled using a rod 74 and a male thread (not shown) on one thumbpad extending into a female thread within the opposite thumbpad. Rod 74 may alternatively be on either right thumbpad 42 or left thumbpad 44. Rod 74 is depicted on left thumbpad 44 in FIG. 2. Rod 74 of left thumbpad 44 extends through tube thumbpad slots 70, channel thumbpad slots 56, and thumbpad hole 46. Both tube thumbpad slots 70 and channel thumbpad slots 56 fit loosely enough to rod 74 to allow travel of rod 74 along the length of the respective slots. Knob groove 72 keys tube 64 to an adjustment knob 73 (FIG. 1) so that rotation of adjustment knob 73 rotates shaft 18.

FIG. 3 depicts further detail of one of tube thumbpad slots 70. The roughly "L" shaped configuration is inverted, with the horizontal portions 81 of the "L" nearer the top of tube 64. Vertical portions 82 extend perpendicular from the proximal parts of horizontal portions 81. Vertical portions 82 are shown bounded by distal walls 84 and proximal walls 83.

Figure 4:
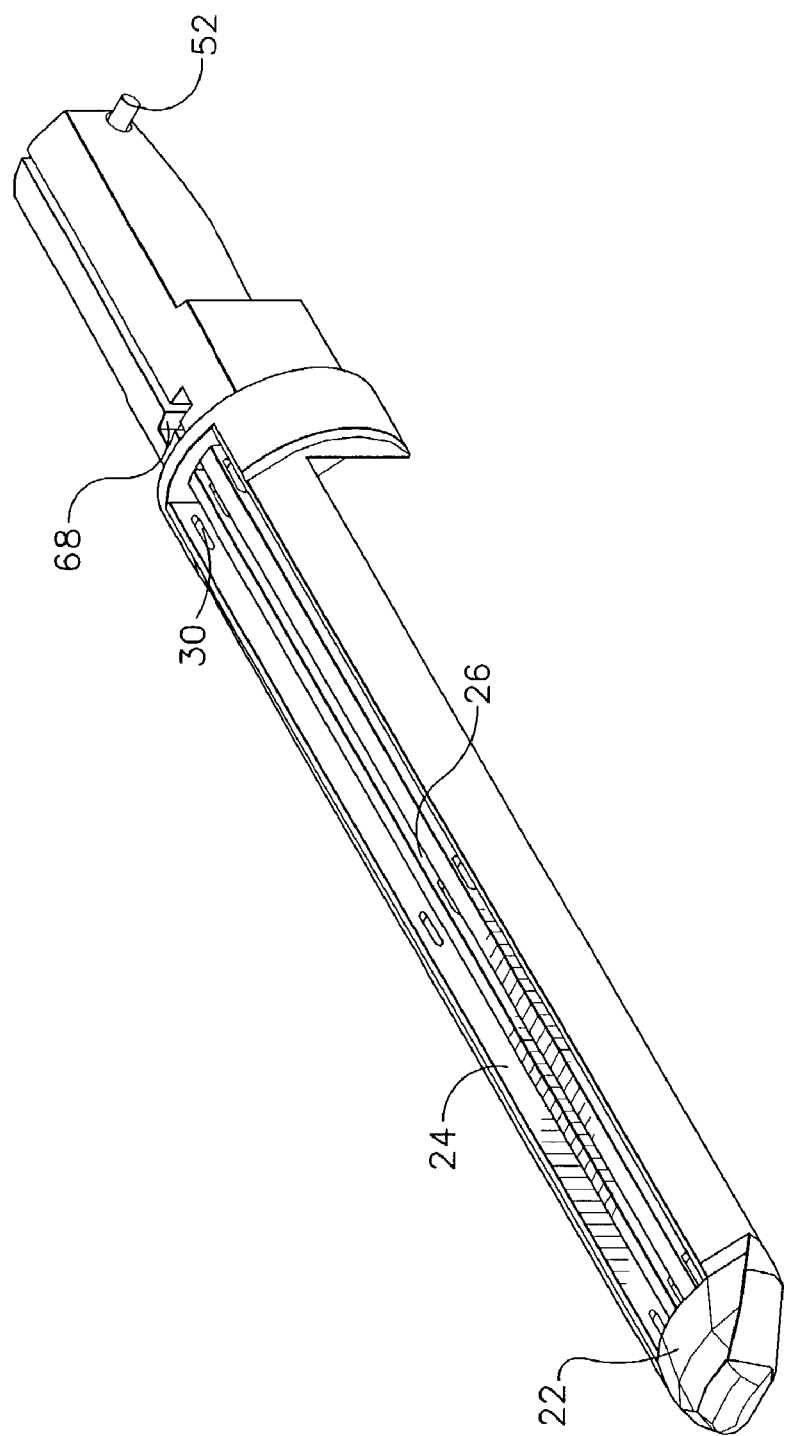
FIG. 4 is an isometric view of the anvil depicted in FIG. 2.

Further detail of anvil 22 is depicted in FIG. 4. Two ribs 26 within cavity 24 fit inside the open portion of the inverted "U" shape of anvil cap 10 to locate anvil cap 10. Anvil slots 30 in anvil 22 align with cap slots 12 when anvil cap 10 is within cavity 24. Anvil pins 40 (FIG. 2) align with and extend through anvil slots 30, anvil holes 36, and cap slots 12. Anvil pins 40 may press through anvil holes 36 in linkage 32. Anvil pins 40 have clearance to move proximally and distally within anvil slots 30. Anvil pins 40 also have clearance to move along the length of diagonal cap slot 12.

FIG. 5 is a side elevation view, partially in section, of shaft 18. In FIG. 5, the configuration of shaft 18 is that of FIG. 1 with anvil 22 closed and anvil cap 10 within cavity 24. On the base of cavity 24, six depressions 28 exist to receive bulges 20 when anvil cap 10 is lowered into cavity 24. It can also be seen that linkage actuator 34, left thumbpad 44, and right thumbpad 42 are moved distally within horizontal portions 81. Linkage actuator 34 will force linkage 32 distally. Linkage 32 moves anvil pins 40 forward, camming against the bottom portion of cap slots 12 to force anvil cap 10 into cavity 24.

FIG. 5 further shows that anvil 22 has an anvil face 21 opposing a cartridge face 29 when anvil 22 and cartridge 60 are approximated. Additionally, anvil cap 10 possesses an anvil cap back side 55. A dimension 23, or height, of the expandable assembly of anvil 22 and anvil cap 10, can be measured from anvil face 21 to anvil cap back side 55 in a direction perpendicular to longitudinal axis 21.

Channel 48 carries a channel back side 57 opposite cartridge face 29. An analogous dimension to dimension 23 could be measured from channel back side 55 to cartridge face 29.

FIG. 6 is a cross-sectional view of anvil 22 taken along line 6—6 of FIG. 5. FIG. 6 depicts anvil cap 10 recessed within cavity 24 of anvil 22. With anvil cap 10 recessed into anvil 22, anvil 22 has a first cross-sectional area and a first area moment of inertia lower than a second cross-sectional area and a second area moment of inertia that can be attained by expanding anvil cap 10 from cavity 24. The dimension 23, or height, of anvil 22 is relatively small, and anvil 22 has first stiffness lower than a second stiffness that can be attained by expanding anvil cap 10 from cavity 24. However, with anvil cap 10 within cavity 24 of anvil 22, in the position shown in FIG. 6, anvil 22 has a low profile easily inserted through a small opening of, for example, a trocar cannula used in endoscopic surgery.

FIG. 7 is a side elevation view, partially in section, of shaft 18 with anvil 22 closed to a position adjacent cartridge 60, and anvil cap 10 moved out of cavity 24. After inserting shaft 18 through an orifice, the physician can raise anvil cap 10 from cavity 24 by moving either left thumbpad 44 or right thumbpad 42 proximally along horizontal portions 81 of tube thumbpad slots 70 as shown in the figure. Left thumbpad 44 or right thumbpad 42 pulls linkage actuator 34 proximally, and linkage actuator 34 in turn moves linkage 32 proximally. Anvil pins 40 exert a force against cap slots 12 to cam anvil cap 10 away from cavity 24 in a direction perpendicular to longitudinal axis 27. Anvil cap 10 is restrained from moving proximally by the proximal wall of cavity 24. After raising anvil cap 10, the user can move either left thumbpad 44 or right thumbpad 42 in a direction away from horizontal portions 81 and along vertical portions 82, rotating linkage actuator 34 slightly relative to linkage 32. Distal walls 84 of tube thumbpad slots 70 restrain left thumbpad 44 and right thumbpad 42 from moving distally, locking anvil cap 10 in the expanded position away from cavity 24.

FIG. 8 is a cross-sectional view of anvil 22 taken along line 8—8 of FIG. 7. FIG. 8 shows anvil cap 10 expanded from cavity 24 of anvil 22. With anvil cap 10 expanded from anvil 22, anvil 22 has a second cross-sectional area and a second area moment of inertia higher than the first cross-sectional area and the first area moment of inertia that exists when anvil cap 10 is lowered into cavity 24. The dimension 23, or height, of anvil 22 has increased, and anvil 22 has a second stiffness higher than the first stiffness that exists when anvil cap 10 is lowered into cavity 24. The size of anvil 22 has effectively increased in a direction perpendicular to longitudinal axis 27. Anvil 22, which had a low profile for easy insertion through a small orifice, now has a higher, stiffer profile for use within a body.

Figure 9:
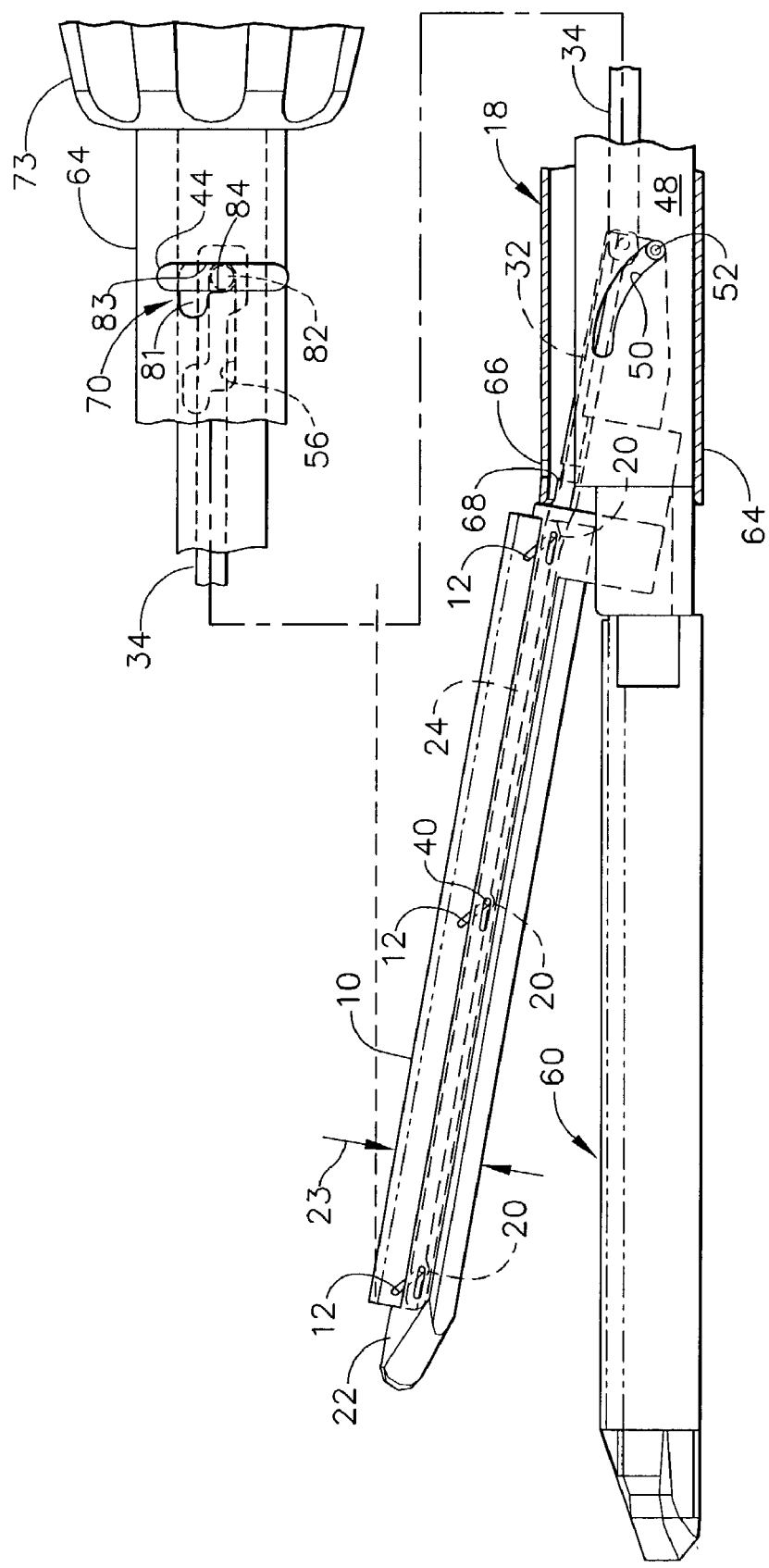
FIG. 9 is a side elevation view, partially in section, of the shaft of the linear cutter of FIG. 1 showing the anvil opened away from the cartridge and the anvil cap raised from the cavity of the anvil.

FIG. 9 shows a split section view of shaft 18 with anvil 10 moved to an open position away from cartridge 60. Closure actuator 41 (FIG. 1) of handle 76 moves tube 64 proximally to open anvil 22 by moving anvil 22 rotatably away from cartridge 60. Pulling tube 64 proximally causes indentation 66 to force anvil 22 proximally by pulling on groove 68. Anvil 22 rotates to an open position when anvil bosses 52 translate along curvilinear slots 50. Tube thumbpad slots 70 move with tube 64 proximally relative to channel thumbpad slots 56. Distal walls 84 on tube 64 urge right thumbpad 42 and left thumbpad 44 proximally through channel thumbpad slots 56. Right thumbpad 42 and left thumbpad 44 draw linkage actuator 34 and linkage 32 proximally, so that linkage actuator 34 maintains a force on anvil cap 10 through anvil pins 40 and cap slots 12. The force maintains anvil cap 10 in a position raised from cavity 24 of anvil 22 as anvil 22 is moved from the closed position to an open position. Linkage 32 also rotates relative to linkage actuator to allow rotation of anvil 22 as anvil bosses 52 translate along curvilinear slots 50.

Opened surgical device 78 may now grasp on tissue requiring transection and stapling. Firing actuator 47 (FIG. 1) within handle 76 can move wedge driver 63 distally to force firing wedge 62 through cartridge 61 to eject staples 61. Pockets in anvil 22 form staples 61 to retain tissue to control bleeding. Knife 65 may be used to transect tissue.

After transection and stapling, the user can remove surgical device 78 from the patient's body through a small orifice. To accomplish removal, the user opens surgical device 78 to unclamp it from any tissue. The user then reverses the procedure depicted in FIGS. 5 through 9. Anvil 22 is first closed by moving tube 64 distally. Distal movement of tube 64 causes the proximal walls 83 of tube thumbpad slots 70 to force right thumbpad 42 and left thumbpad 44 distally through channel thumbpad slots 56. Right thumbpad 42 and left thumbpad 44 move to the distal sections of channel thumbpad slots 56, where the vertical portions 82 of channel thumbpad slots 56 become available for use. Moving either thumbpad first vertically along vertical portions 82, then horizontally and distally along horizontal portions 81 after the thumbpads are in the distal position will return the thumbpads to the original position depicted in FIG. 3 and lower anvil cap 10 into cavity 24. The closed anvil 22 with retracted anvil cap 10 may now be withdrawn through a smaller orifice that would be possible with expanded anvil 22.

It will be recognized that equivalent structures may be substituted for the structures illustrated and described herein and that the described embodiment of the invention is not the only structure which may be employed to implement the claimed invention. As one example of an equivalent structure that may be used to implement the present invention, the endoscopic linear cutter may be a surgical implement such as a grasper, scissors, or other endoscopic surgical tools. Anvil cap 10 may be a plate that moves alongside an end-effector of a surgical tool instead of recessing into a cavity in the end-effector.

While preferred embodiments of the present invention have been shown and described herein, it will be obvious to those skilled in the art that such embodiments are provided by way of example only. For example, as would be apparent to those skilled in the art, the disclosures herein have equal application in robotic or power assisted surgery. In addition, it should be understood that every structure described above has a function and such structure can be referred to as a means for performing that function. Numerous variations, changes, and substitutions will now occur to those skilled in the art without departing from the invention. Accordingly, it is intended that the invention be limited only by the spirit and scope of the appended claims.

What is claimed is:

1. A surgical stapling device for stapling tissue with a plurality of staples, said stapling device comprising:
   a. an elongated shaft having a proximal end and a distal end extending therefrom, and an elongated end effector having a proximal end attached to said distal end of said shaft, a distal end extending therefrom and a longitudinal axis extending therebetween;
   b. said end effector comprising a first jaw having a plurality of staples therein and a second jaw, opposing said first jaw, having an anvil thereon said jaws movable with respect to each other from an open position, wherein the jaws are spaced apart, to a closed position wherein the jaws are in close approximation to one another;
   c. at least one of said jaws having an expandable member on a back side thereof for selectively increasing a height of said at least one jaw.

2. The surgical device according to claim 1 wherein said expandable member is sized such that when it expands it increases an area moment of inertia of a cross-section of said second jaw.

3. The surgical device of claim 1 wherein said device further includes an expander actuator for selectively expanding said expandable member, said actuator being proximal to said end effector.

4. The surgical device of claim 1 wherein said expandable member is substantially rigid.

5. The surgical device of claim 1 further including a handle attached to said proximal end of said shaft.

* * * * *